United States Patent
Rice et al.

(10) Patent No.: US 8,496,668 B2
(45) Date of Patent: Jul. 30, 2013

(54) COMBINED UMBILICAL CORD CUTTER, CLAMP, AND DISINFECTANT

(75) Inventors: David Rice, New Orleans, LA (US); William Kethman, Houston, TX (US); Bryan Molter, St. Louis, MO (US); Stephanie Roberts, Indianapolis, IN (US); Mark Young, St. Louis, MO (US)

(73) Assignee: The Adminstrators of the Tulane Educational Fund, New Orleans, LA (US)

(*) Notice: Subject to any disclaimer, the term of this patent is extended or adjusted under 35 U.S.C. 154(b) by 107 days.

(21) Appl. No.: 12/506,799

(22) Filed: Jul. 21, 2009

(65) Prior Publication Data

US 2010/0137877 A1    Jun. 3, 2010

Related U.S. Application Data

(60) Provisional application No. 61/135,465, filed on Jul. 21, 2008.

(51) Int. Cl.
*A61B 17/42*    (2006.01)

(52) U.S. Cl.
USPC ............................................. 606/120; 30/134

(58) Field of Classification Search
USPC ............ 606/120, 142, 174, 157, 167; 30/124, 30/134
See application file for complete search history.

(56) References Cited

U.S. PATENT DOCUMENTS

| | | |
|---|---|---|
| 4,716,886 A | 1/1988 | Schulman et al. |
| 4,938,215 A | 7/1990 | Schulman et al. |
| 5,667,516 A * | 9/1997 | Allen ............................ 606/120 |
| 5,676,672 A * | 10/1997 | Watson et al. ................ 606/120 |
| 5,817,103 A | 10/1998 | Bell |
| D455,832 S | 4/2002 | Watson, Jr. et al. |
| 6,443,958 B1 | 9/2002 | Watson, Jr. et al. |
| 7,307,530 B2 * | 12/2007 | Fabian et al. .............. 340/572.1 |

* cited by examiner

*Primary Examiner* — Victor Nguyen
(74) *Attorney, Agent, or Firm* — Baker, Donelson, Bearman, Caldwell & Berkowitz, P.C.

(57) ABSTRACT

Provided is a combined umbilical cord clamp, cutter, disinfectant, and data collecting system which reduces the risk of cord infections due to unsanitary birth conditions. Also provided is an identification system which aids in the collection of birth statistics.

21 Claims, 9 Drawing Sheets

COMBINED UMBILICAL CORD CUTTER, CLAMP, AND DISINFECTANT

CROSS-REFERENCES TO RELATED APPLICATIONS

This Non-Provisional Patent Application, filed under 35 U.S.C. §111(a), claims the benefit under 35 U.S.C. §119 (e)(1) of U.S. Provisional Patent Application No. 61/135,465, filed under 35 U.S.C. §111(b) on 21 Jul. 2008, and which is hereby incorporated by reference in its entirety.

STATEMENT REGARDING FEDERALLY SPONSORED RESEARCH

Not applicable.

COMPACT DISK SUBMISSION

Not applicable.

BACKGROUND OF THE INVENTION

1. Field of the Invention

The present invention relates to a combined umbilical cord clamp, cutter, disinfectant, and data collecting system which reduces the risk of cord infections due to unsanitary birth conditions and also provides an identification system which aids in the collection of birth statistics.

2. Description of Related Art

Infections represent one of the most common complications of childbirth. Even in developed countries, individual cases and epidemics of cord infections continue to occur. In developing nations where health care infrastructure is commonly limited and inadequate, most deliveries occur outside a hospital setting with help from family or traditional birth attendants. Two-thirds of neonatal deaths worldwide occur in Africa and Southeast Asia, where traditional birth practices involve severing the cord using non-sterile instruments that often lead to infection. This is due not only to poor access to quality care but also socio-cultural behaviors. In many cultures, some type of ritual substance is applied to the cord stump. Ash, oil, butter, spice pastes, herbs, mud, and cow or chicken dung are commonly used, and they are often contaminated with bacteria and spores. This practice of applying substances to the cord is most commonly employed to prevent bleeding, to promote separation of the stump, and to keep spirits away. With such unsanitary conditions, there exists a much higher rate of infant mortality due to preventable causes, such as bacterial infections and neonatal tetanus. The lack of research efforts targeted at birth conditions outside of hospitals in developing nations has simultaneously prevented the development of effective, affordable, and feasible preventative strategies that could be widely applied towards neonatal health.

The first few weeks of a newborn mammal's life are critical to its long-term survival and health. Umbilical cord care is just as important in veterinary use as it is in human use, especially since the environment an animal is born into is usually less sterile than that of a human birth. The umbilical cord is usually severed immediately after a birth, and typically a disinfectant is applied to prevent pathogens from entering an animal's body through the cord. Umbilical cord devices are rarely used in veterinary medicine, even though they could be equally as beneficial in helping to prevent infection. Large animal births, in particular, could benefit from an improved means of severing, disinfecting, and covering the umbilical cord, as many large animal births are not attended by a trained veterinarian but by a livestock handler.

An additional difficulty in improving neonatal health is the lack of accurate, reliable and up-to-date data. When data is available, its usefulness is often questioned, with concerns related to limited coverage and poor quality of collection. Often times, birth estimates are extrapolated from data collected outside of the areas and settings of interest. A need exists for a disposable, sterile, and comprehensive clamping and cutting device for the severing of the umbilical cord that would also aid in collecting data on birth rates through the use of an automatic identification method. Currently, identification methods such as radio-frequency identification (RFID) tags are gaining popularity in many hospitals, whereby wrist or ankle bracelets are placed on the mother and infant. However, integration of an identification method into a medical device eliminates the extra step of placing a tag on the newborn during the chaotic period after a birth, and it could prevent a mother/baby mix-up in the hospital setting when a baby is sent to the wrong mother after being separated for neonatal care. This could also apply to domesticated mammals by providing an identification method early in the animal's life before a more permanent form of identification is implemented.

Currently, there is limited support for research that focuses on the preventable causes of neonatal infection and death. A key disadvantage of the present umbilical cord cutting method is its multi-step nature; the procedure of severing the umbilical cord involves three pieces of equipment: two clamps and a cutter. In practice, two metal clamps are secured to the umbilical cord in a spaced relation to one another, and the cord is then cut between the two clamps using scissors. The metal clamp on the baby's side is then replaced with a plastic clamp and the other is removed when the placenta is discarded. Outside of the hospital, the method for severing the umbilical cord often involves the use of tying devices, usually a type of string, to stop the flow of blood and a sharp blade, often contaminated, to sever the cord between the two points. Additionally, cutting the cord at an intermediate distance between two clamps leaves an edge of the cord past the clamp, which is a prime site for infection.

Various surgical instruments have been developed to separate and clamp the umbilical cord joining a newborn infant and the mother. However, most are reusable, which presents additional health concerns due to the possibility of contamination and infection; those that claim not to be reusable still utilize a metallic cutting device that could be easily removed and reused. The metallic blade is problematic for three reasons: it is a safety hazard, there is a risk of the blade being removed for reuse, and it is less economical to manufacture. In addition, variations on obstetric scissors do not provide adequate protection from blood splatter, placing the birth attendant at risk from contracting Hepatitis B, Hepatitis C, and Human Immunovirus. Furthermore, it is usually necessary to first orient the device so that the clamp side with the blade remains on the mother's side of the cord to be discarded with the placenta. Improper orientation of such devices is more likely to occur in developing nations because language barriers and low levels of literacy will limit the effectiveness of providing instructions for proper use. This type of mistake may leave the wrong side of the device with the newborn, possibly resulting in infection and various other complications.

An initial application of antimicrobials onto the stump of the umbilical cord can contribute to protection against neonatal tetanus, especially in the first three days of life where the stump of the umbilical cord may be exposed to environmental contaminants. In addition, application of antimicrobials onto the umbilical stump can reduce the risk of sepsis, which is a major cause of infant death in developing countries. Prevention of neonatal tetanus and other infections remains a challenge in spite of the availability of vaccines and agency efforts to train birth attendants in cord-care practices. Topical antimicrobials applied to the stump of the umbilical cord can provide additional benefits to a vaccine program or to a situation where such a program is not well established. Topical agents are easy to distribute and use; however, when an antimicrobial is applied by the traditional birth attendant or the mother, it may not be applied appropriately in a sterile environment. Therefore, a device which incorporates an antimicrobial into the design would be very beneficial. Further, plastic materials used in the medical field can easily be colonized by microorganisms, whether the birth occurs inside or outside of a hospital. In areas with a high incidence of neonatal tetanus and sepsis, an umbilical cutting device that incorporates an antimicrobial plastic could reduce the risk of infections of the umbilical stump.

The present invention provides an efficient and user-friendly device to simultaneously clamp, cut, and disinfect the umbilical cord and also to provide a method of data collection and identification. The design of this device focuses on ease of use, whereby an unskilled person can safely and effectively cut an umbilical cord. To decrease manufacturing costs, each device will be made entirely of plastic, including the cutting mechanism. A symmetrical design allows the orientation of the device to be irrelevant during use, which further decreases its complexity. That is, the side of the device that the birth attendant faces towards the infant is irrelevant. Each device will either contain a disinfectant packet that will be severed simultaneously with the umbilical cord, or the device will be made of an antimicrobial plastic to provide a sterilized environment for the cord. Each clamp/cutter piece slides apart along the axis of the cord, and one of the clamp/cutters remains with the infant. Thus, the detached clamp protects and eliminates access to the umbilical stump wound, containing the cut umbilical cord until it atrophies and falls off. A minimum of one locking mechanism is incorporated to ensure that the device cannot be reopened.

Further embodiments of this invention provide a birth identification method for developing nations through the use of passive RFID tags embedded in each clamping/cutting constituent. After a birth and the use of the device to sever the umbilical cord of a newborn, the detached clamping/cutting constituent not remaining with the infant can be taken to a collection center. As an incentive, the separated component acts as a token, and could be exchanged for essential supplies such as baby formula, food, or necessary vaccinations. With the collected device containing the RFID tag, a computer can collect data on the number of births in a particular area.

Another embodiment of this invention provides a birth identification method for developed nations and veterinary applications through the use of RFID tags embedded in each clamping/cutting constituent. Any mother/baby or owner/animal mix-up is a potential liability to a hospital; therefore, an RFID system can increase safety and ensure security of a newborn. After a birth, the device can be used to track the newborn effectively linking the mother to the child, which will help in cases of child theft or hospital mix-ups. This technology could also provide valuable birth statistics.

While certain novel features of this invention shown and described below are pointed out in the annexed claims, the invention is not intended to be limited to the details specified, since a person of ordinary skill in the relevant art will understand that various omissions, modifications, substitutions and changes in the forms and details of the device illustrated and in its operation may be made without departing in any way from the spirit of the present invention. No feature of the invention is critical or essential unless it is expressly stated as being "critical" or "essential."

BRIEF SUMMARY OF THE INVENTION

The present invention relates to a disposable, comprehensive unit that simultaneously clamps, cuts, and disinfects the stump of the umbilical cord in an easy-to-use motion, thus reducing the likelihood of exposure to infectious organisms and mistakes made by untrained delivery personnel. The preferred deployment of this invention is for use in areas where health infrastructure is inadequate and inaccessible. An alternative deployment of this invention is for use in developed nations, where cord infection is still prevalent. By employing preventative measures and a more sterile environment, application of this device in these settings would help to reduce infant mortality and the spread of infectious disease during delivery and also provide a method for baby tracking, identification, and collection of birth data.

DETAILED DESCRIPTION OF THE INVENTION

Figure 1:
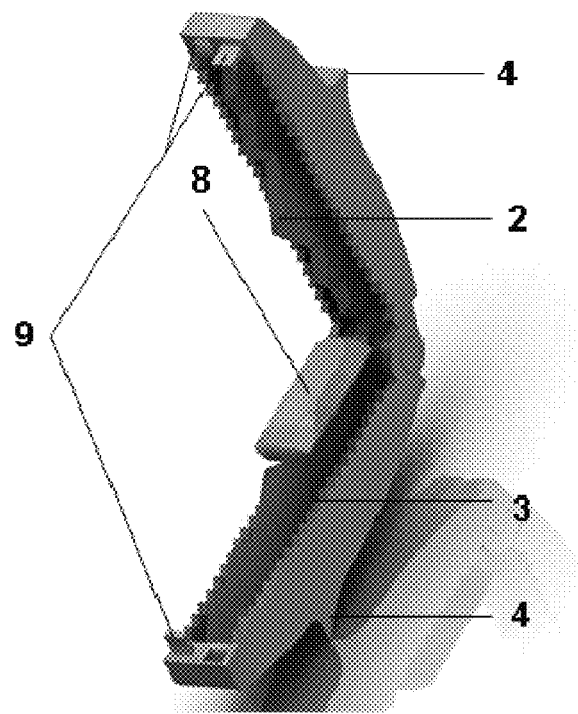
FIGS. 1, 2, 3 and 4 illustrate the preferred embodiment of the present invention, which includes the following components as labeled in FIGS. 1, 2, 3 and 4: (1) Two symmetric units, thin and oval-shaped, composed of a hard plastic material embedded with an RFID chip and that is sufficient to cut umbilical tissue; (2) A saw-toothed, chamfered cutting blade; (3) A clamp with smaller, curved saw-toothed edges that close to form a tight seal around the umbilical cord tissue; (4) An ergonomically designed handle-grip, located midway along the length of the symmetric units, formed by the shape of the units and intended for one-handed, ambidextrous use; (5) A barrel hinge to allow the device to be manufactured as two symmetric parts; (6) A ratchet-locking system incorporated with the hinge to prevent the symmetric units from being reopened after use; (7) Simple press fit extrusions, which temporarily hold the two symmetric units together until the umbilical cord has been severed; (8) A small disinfectant packet located between the blades; and (9) A hook-locking mechanism to ensure the device does not reopen once the cutting motion is complete.
Figure 2:
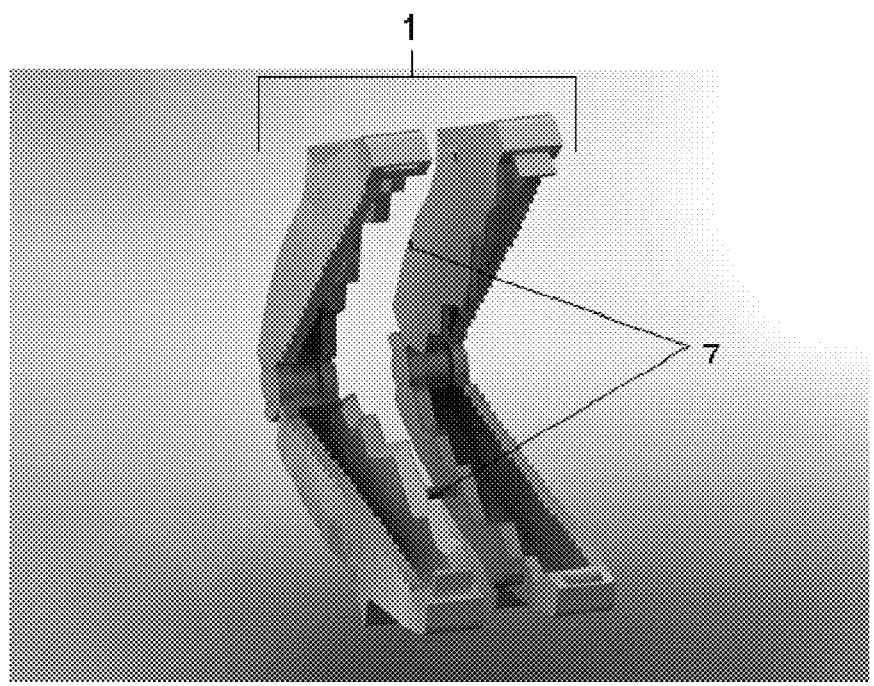
Figure 3:
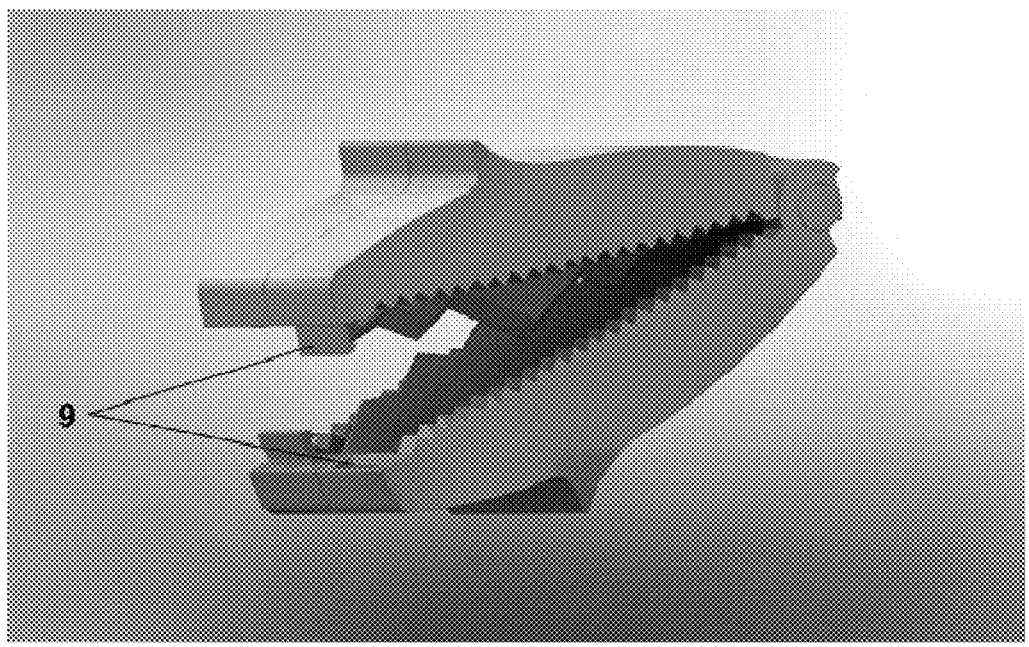
Figure 4:
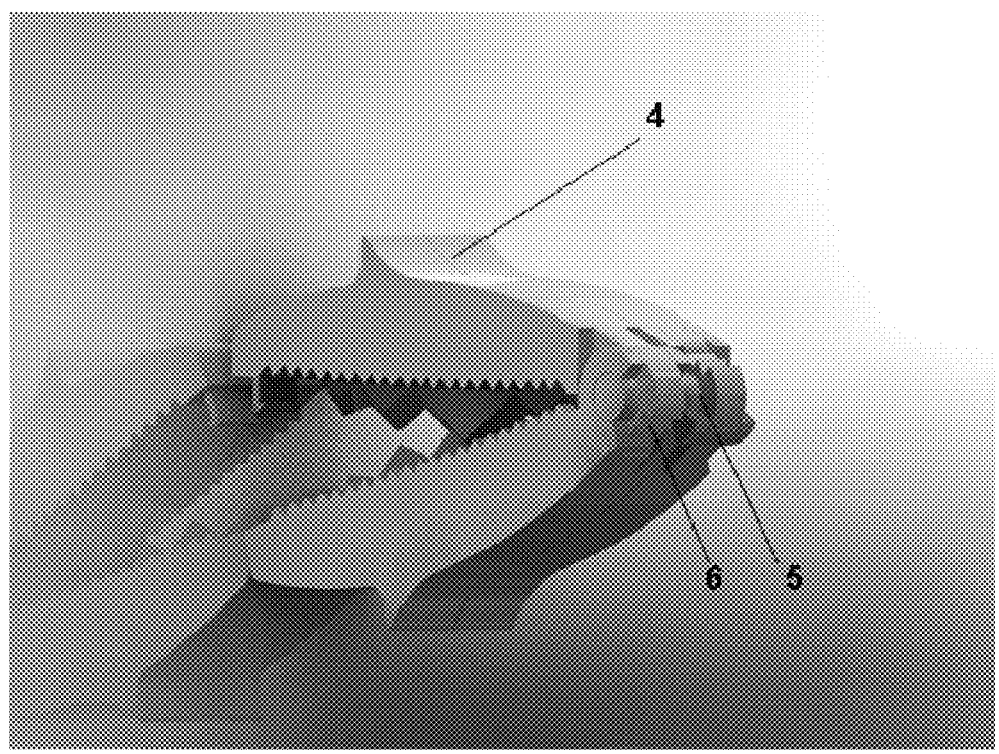

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

The present invention encompasses three embodiments of a combined umbilical cord clamp, cutter, disinfectant, and data collecting system to be used in developing nations (FIG. 1, FIG. 2, FIG. 3, FIG. 4, FIG. 5, FIG. 6, FIG. 7, FIG. 8, and FIG. 9).

In the first embodiment illustrated in FIGS. 1, 2, 3, and 4, two symmetric units composed of a sufficiently hard plastic material to cut umbilical tissue and embedded with an RFID chip fit together and form a thin, oval shape (1). This guides the umbilical tissue to the center of the device, producing an even cutting motion as the device is being closed. The use of two identical units allows the orientation of the device to be irrelevant during use.

Each unit has a saw-toothed chamfered cutting blade with the largest blade in the center to allow the largest cut to be made in the center of the umbilical cord (2). The chamfered edges of the blade provide shearing strength, thereby allowing the blade to be manufactured in the same hard plastic as the rest of the device (1). Once closed, the chamfered edge produces a seal, preventing the umbilical cord from being exposed to the environment. The blades of the symmetric units are flush with one another when the units are together, creating a single cutting site along the umbilical cord.

Each unit also has a clamp (3) with small, curved saw-toothed edges. Once closed, these edges form a tight seal around the umbilical cord tissue to stop the flow of blood. Unlike the cutting blade (2), the teeth of the clamp are dulled in order to securely clamp the cord without severing it.

An ergonomically designed handle-grip (4) flares out from the curve of the symmetric units (1). The placement of the handle gives the user extra leverage during the cutting stroke to ensure that the umbilical cord is completely severed. It also provides an obvious gripping point; the shape of the handle allows the user's thumb to rest in the curved portion on one side and the user's index finger to rest in the curved portion on the other side.

Each unit has a barrel hinge, allowing the device to be manufactured as two symmetric parts (5). The two hinges of the symmetric units are in parallel to provide a single axis of rotation for a smooth cutting motion.

The ratchet-locking system (6) is incorporated with the barrel hinge (5). Once closure of the device begins, the ratchet-locking system prevents the symmetric units from being reopened after use. With each small movement toward closing the device, successive ratchet locks will take hold and prevent the device from being opened wider than the current position. This is important because reopening would nullify many of the safety and disinfectant features of the device.

The press fit extrusions (7) temporarily hold the two symmetric units together until the umbilical cord has been severed. After cutting, the units are pulled apart to form separate entities, and one unit remains attached to the infant until the stump of the umbilical cord atrophies and falls off.

The symmetric units contain a small disinfectant packet located between the two blades (8). In one motion, the blade travels through the packet, severing the cord and releasing the contents onto the severed end of the umbilical cord.

The hook-locking mechanism ensures the device does not reopen once the cutting motion is complete (9). This feature is a failsafe for the ratchet lock (6), and together, the two features comprise a tamper-proof locking system.

Figure 5:
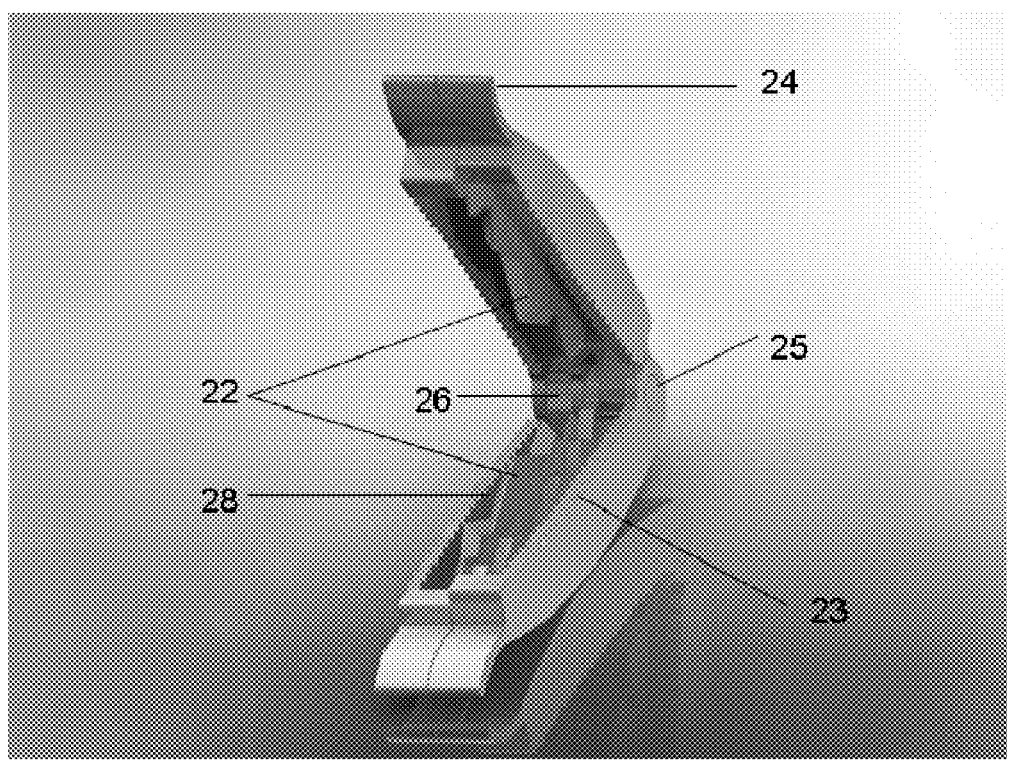
FIGS. 5 and 6 illustrate an alternative embodiment of the present invention, which includes the following components as labeled in FIGS. 5 and 6: (21) Two symmetric units, thin and S-shaped, composed of a hard plastic material embedded with an RFID chip and that is sufficient to cut umbilical tissue; (22) A saw-toothed, chamfered cutting blade with a semi-circular shape to allow for an even cutting motion; (23) A clamp with smaller saw-toothed edges that close to form a tight seal around the umbilical cord tissue; (24) An ergonomically designed handle formed by the shape of the units and intended for one-handed, ambidextrous use; (25) A barrel hinge to allow the device to be manufactured as two symmetric units; (26) A ratchet-locking system incorporated with the hinge to prevent the symmetric units from being reopened after use; (27) Simple press fit extrusions, which temporarily hold the two symmetric units together until the umbilical cord has been severed; and (28) A small reservoir providing space for a disinfectant packet.
Figure 6:
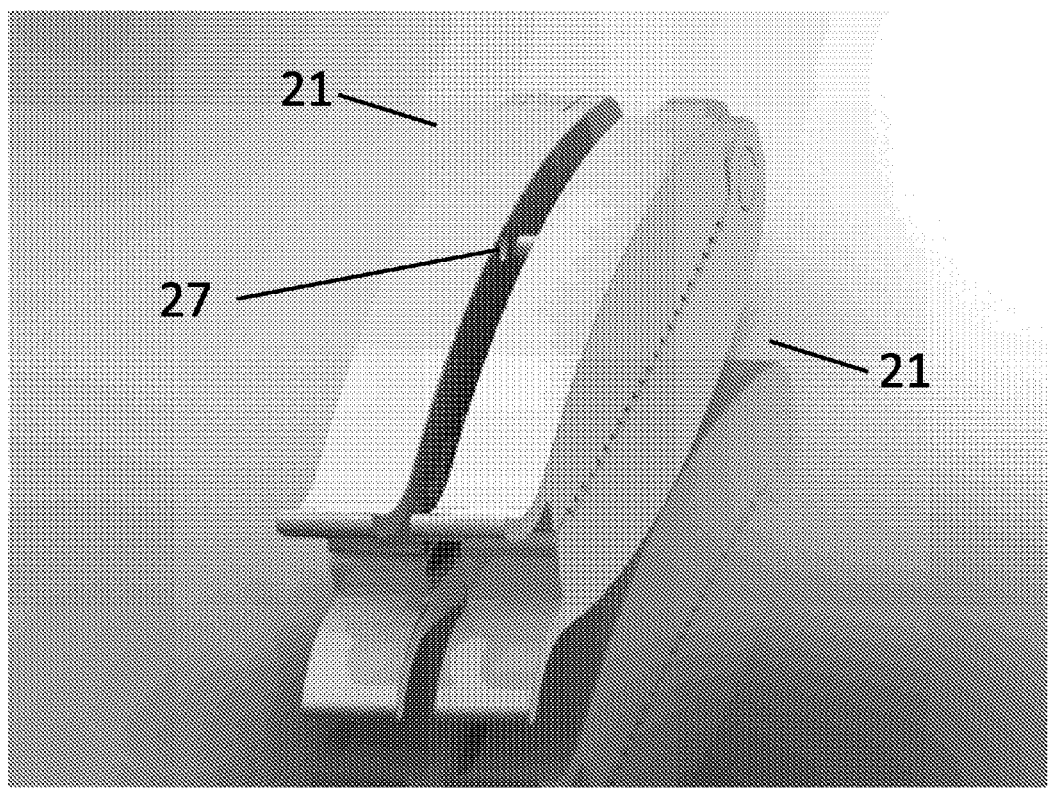

In the second embodiment illustrated in FIGS. 5 and 6, two symmetric units composed of a sufficiently hard plastic material to cut umbilical tissue embedded with an RFID chip fit together to form a thin, S-curved shape (21). This guides the umbilical tissue to the center of the device, producing an even cutting motion as the device is being closed. The use of two identical units allows the orientation of the device to be irrelevant during use.

Each unit has a saw-toothed chamfered cutting blade with a semi-circular shape to allow for an even cutting motion (22). The chamfered edges of the blade provide shearing strength, thereby allowing the blade to be manufactured in the same hard plastic as the rest of the device (21). Once closed, the chamfered edge produces a seal, preventing the umbilical cord from being exposed to the environment. The blades of the symmetric units are flush with one another, creating a single cutting site along the umbilical cord.

Each unit also has a clamp (23) with small saw-toothed edges. Once closed, these edges form a tight seal around the umbilical cord tissue to stop the flow of blood. Unlike the cutting blade (22), the teeth of the clamp are dulled in order to securely clamp the cord without severing it.

An ergonomically designed handle (24) is formed by the S-curved shape of the two symmetric units (21). The placement of the handle gives the user extra leverage at the end of the cutting stroke to ensure that the umbilical cord is completely severed. It also provides an obvious gripping point; the shape of the handle allows the user's thumb to rest in the curved portion on one side and the user's index finger to rest in the curved portion on the other side.

Each unit has a barrel hinge, allowing the device to be manufactured as two symmetric parts (25). The two hinges of the symmetric units are in parallel to provide a single axis of rotation for a smooth cutting motion.

The ratchet-locking system (26) is incorporated with the barrel hinge (25). Once closure of the device begins, the ratchet-locking system prevents the symmetric units from being reopened after use. With each small movement toward closing the device, successive ratchet locks will take hold and prevent the device from being opened wider than the current position. This is important because reopening would nullify many of the safety and disinfectant features of the device.

The press fit extrusions (27) temporarily hold the two symmetric units together until the umbilical cord has been severed. After cutting, the units are pulled apart to form separate entities, and one unit remains attached to the infant until the stump of the umbilical cord atrophies and falls off.

The symmetric units contain a small reservoir, providing space for a disinfectant packet (28). In one motion, the blade travels through the packet during the cutting motion, releasing the contents onto the severed end of the umbilical cord.

Figure 7:
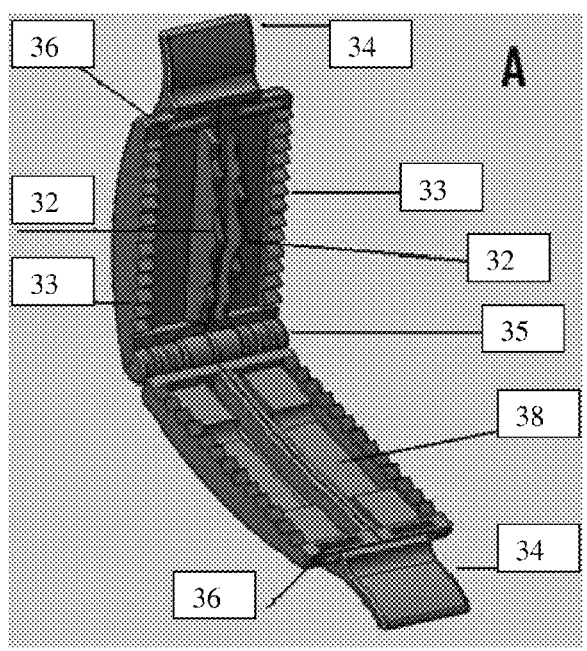
FIGS. 7, 8 and 9 illustrate an alternative embodiment of the present invention, which includes the following components as labeled in FIG. 3: (31) Two symmetric units, thin and oval-shaped, composed of a hard plastic material embedded with an RFID chip and that is sufficient to cut umbilical tissue; (32) A saw-toothed, chamfered cutting blade with a semi-circular shape to allow for an even cutting motion; (33) A clamp with smaller saw-toothed edges that close to form a tight seal around the umbilical cord tissue; (34) A separate S-shaped, ergonomically designed handle that wraps around the two symmetric units and is intended for one-handed, ambidextrous use; (35) A barrel hinge to reduce the number of parts in the manufacturing process; (36) A hook-locking mechanism to ensure the device does not reopen once the cutting motion is complete; (37) Four flared locking bars that allow the two symmetric units to slide out of the handled holder; and (38) A small reservoir providing space for a disinfectant packet.
Figure 8:
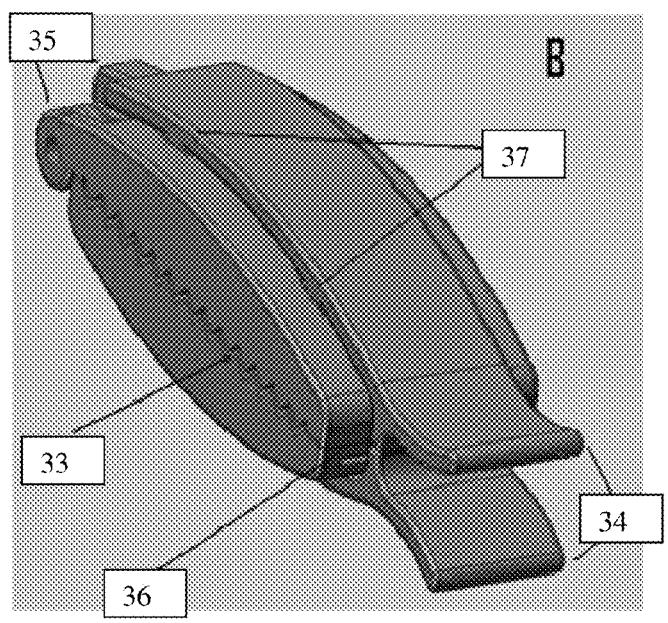
Figure 9:
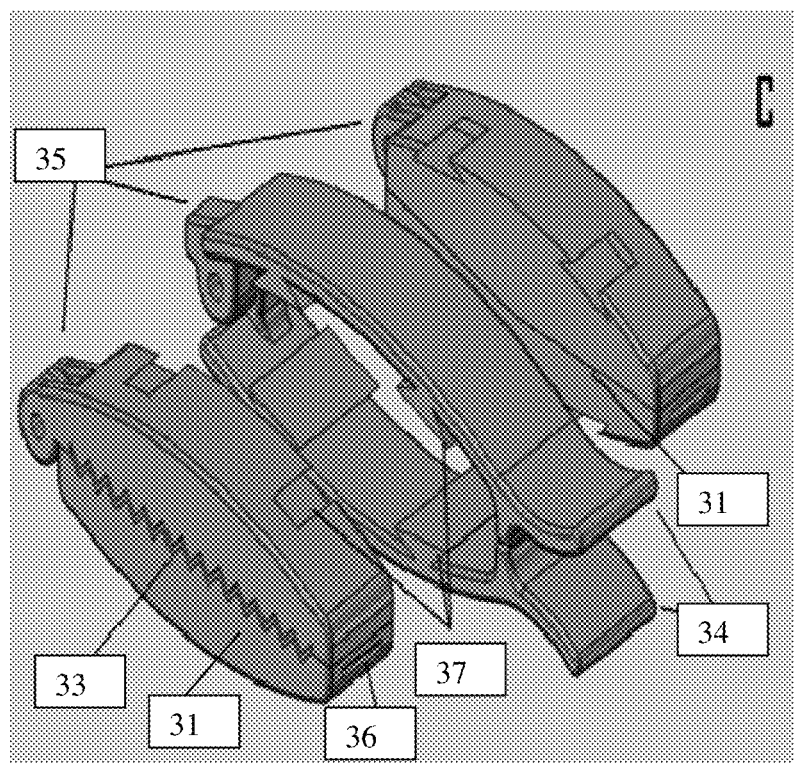

In the third embodiment illustrated in FIGS. 7, 8 and 9, two symmetric units composed of a sufficiently hard plastic material to cut umbilical tissue embedded with an RFID chip fit together and form an oval shape (31). This guides the umbilical tissue to the center of the device, producing an even cutting motion as the device is being closed. The use of two identical units allows the orientation of the device to be irrelevant during use.

Each unit has a saw-toothed chamfered cutting blade with a semi-circular shape to allow for an even cutting motion (32). The chamfered edges of the blade provide shearing strength, thereby allowing the blade to be manufactured in the same hard plastic as the rest of the device (31). Once closed, the edge of each unit produces a seal, preventing the umbilical cord from being exposed to the environment. Each blade is completely enclosed by its respective symmetric unit; therefore, there are two cutting sites along the umbilical cord.

Each unit also has a clamp (33) with small saw-toothed edges. Once closed, these edges form a tight seal around the umbilical cord tissue to stop the flow of blood. Unlike the cutting blade (32), the teeth of the clamp are dulled in order to securely clamp the cord without severing it.

A separate ergonomically designed handle forms an S-curved shape around the two symmetric units (34). The placement of the handle gives the user extra leverage at the end of the cutting stroke to ensure that the umbilical cord is completely severed. It also provides an obvious gripping point; the shape of the handle allows the user's thumb to rest in the curved portion on one side and the user's index finger to rest in the curved portion on the other side. The separate handle also provides added protection from umbilical blood that could leak through the space between the symmetric units (31).

Each unit has a barrel hinge to reduce the number of manufacturing parts (35). The two hinges of the symmetric units and the hinge of the handled holder are all in parallel to provide a single axis of rotation for a smooth cutting motion.

The hook locking system ensures the device does not reopen once the cutting motion is complete (36). This is important because reopening would nullify many of the safety and disinfectant features of the device.

Four flared locking bars allow the two symmetric units to slide out of the handled holder (37). After cutting, the units are pulled apart to form separate entities, and one unit remains attached to the infant until the stump of the umbilical cord atrophies and falls off.

The symmetric units contain a small reservoir, providing space for a disinfectant packet (38). In one motion, the blade travels through the packet during the cutting motion, releasing the contents onto the severed end of the umbilical cord.

The following is a list of reference numerals for FIGS. 1, 2, 3 and 4:

List for Reference Numerals

FIGS. 1, 2, 3 and 4

| | |
|---|---|
| 1 | Symmetric Units |
| 2 | Cutting Blade |
| 3 | Clamp |
| 4 | Handle Grip |
| 5 | Barrel Hinge |
| 6 | Ratchet Locking System at the hinge |
| 7 | Press Fit Extrusions to temporarily hold two units together |
| 8 | Disinfectant Packet |
| 9 | Hook Locking Mechanism |

The following is a list of reference numerals for FIGS. 5 and 6:

List for Reference Numerals

FIGS. 5 and 6

| | |
|---|---|
| 21 | Symmetric Units |
| 22 | Cutting Blade |
| 23 | Clamp |
| 24 | Handle |
| 25 | Barrel Hinge |
| 26 | Ratchet locking system at the hinge |
| 27 | Press Fit Extrusions to temporarily hold two units together |
| 28 | Small reservoir for disinfectant packet |

The following is a list of reference numerals for FIGS. 7, 8 and 9:

List for Reference Numerals

FIGS. 7, 8 and 9

| | |
|---|---|
| 31 | Symmetric Units |
| 32 | Cutting Blade |
| 33 | Clamp |
| 34 | Separate Handled Holder |
| 35 | Barrel Hinge |
| 36 | Hook Locking Mechanism |
| 37 | Four Flared Locking Bars to connect units to handled holder |
| 38 | Small reservoir for disinfectant packet |

It will be understood that each of the elements described above, or two or more together may also find a useful application in other types of methods differing from the type described above. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention set forth in the appended claims. The foregoing embodiments are presented by way of example only; the scope of the present invention is to be limited only by the following claims.

The invention claimed is:
1. A device that simultaneously clamps and cuts an umbilical cord, said device comprising two identical units, wherein each unit comprises:
(a) a saw-toothed, chamfered cutting blade;
(b) a clamp comprising curved saw-toothed edges;
(c) an ergonomically designed handle-grip formed by the shape of the two units;
(d) a hinge;
(e) a ratchet locking system located at the hinge;
(f) a press fit extrusion;

(g) a reservoir that provides space for a disinfectant packet, wherein the disinfectant packet is located between the cutting blades.

2. The device of claim 1, in which the device is composed of a sufficiently hard plastic material to cut umbilical tissue.

3. The device of claim 1, in which a radio frequency identification chip is embedded within the device.

4. The device of claim 1, in which the identical units are composed of a plastic with antimicrobial properties.

5. The device of claim 1, in which the two identical units are thin and oval-shaped.

6. The device of claim 1, wherein the handle-grip is located midway along the length of the identical units.

7. The device of claim 1, further comprising a hook locking mechanism.

8. The device of claim 1, in which the device is used on humans.

9. The device of claim 1, in which the device is used on non-human mammals.

10. The device of claim 1, wherein the teeth of the edges in clamp (b) are smaller and duller than blade (a).

11. The device of claim 1, wherein the ergonomically designed handle grip (c) flares out from the curve of the identical units.

12. The device of claim 1, wherein the hinges of the two identical units are in parallel to provide a single axis of rotation.

13. A device comprising a first and a second unit, wherein said units are identical and removably attached to one another, and each unit comprising:
   a) a blade, wherein said blade is centrally-disposed in said device;
   b) a clamp portion comprising opposing saw-toothed edges, wherein said clamp portion is; laterally-disposed in said device;
   c) a hinge movably connecting said opposing saw-toothed edges, the hinge further comprising a ratchet mechanism, whereby said ratchet mechanism prevents separation of the opposing saw-toothed edges after said opposing saw-toothed edges are moved toward one another;
   d) means for removably attaching each said unit to another said unit; and
   e) a locking mechanism separate from said ratchet mechanism whereby the locking mechanism prevents separation of the opposing saw-toothed edges after said opposing saw-toothed edges are brought together.

14. The device of claim 13, in which the device is composed of a sufficiently hard plastic material to cut umbilical tissue.

15. The device of claim 13, in which a radio frequency identification chip is embedded within the device.

16. The device of claim 13, in which the identical units are composed of a plastic with antimicrobial properties.

17. The device of claim 13, further comprising a reservoir that provides space for a disinfectant packet, wherein the disinfectant packet is located between the cutting blades.

18. The device of claim 13, in which the two identical units are thin and oval-shaped.

19. The device of claim 13, wherein the handle-grip is located midway along the length of the identical units.

20. The device of claim 13, further comprising a hook locking mechanism.

21. A biradially symmetrical device that simultaneously clamps, cuts and disinfects an umbilical cord, said device comprising two biradially symmetrical units, wherein each unit comprises:
   (a) a saw-toothed, chamfered cutting blade;
   (b) a clamp comprising curved saw-toothed edges;
   (c) an ergonomically designed handle-grip formed by the shape of the two units;
   (d) a barrel hinge comprising a ratchet mechanism, whereby said ratchet mechanism prevents separation of the opposing saw-toothed edges after said opposing saw-toothed edges are moved toward one another;
   (e) a locking mechanism separate from said ratchet mechanism whereby the locking mechanism prevents separation of the opposing saw-toothed edges after said opposing saw-toothed edges are brought together; and
   (f) a press fit extrusion;
wherein the device comprises plastic having antimicrobial properties, or wherein the device further comprises a disinfectant packet.

* * * * *